United States Patent
Dahlborn

[11] Patent Number: 5,868,142
[45] Date of Patent: Feb. 9, 1999

[54] IMPLANTABLE DEVICE

[75] Inventor: Carl Dahlborn, Lidingö, Sweden

[73] Assignee: Carl Dahlborn AB, Lidingo, Sweden

[21] Appl. No.: 750,065

[22] PCT Filed: Jun. 4, 1995

[86] PCT No.: PCT/SE95/00647

§ 371 Date: Dec. 3, 1996

§ 102(e) Date: Dec. 3, 1996

[87] PCT Pub. No.: WO95/33445

PCT Pub. Date: Dec. 14, 1995

[30] Foreign Application Priority Data

May 6, 1994 [SE] Sweden .................................. 9401919

[51] Int. Cl.$^6$ ............................. A61B 19/00; A61F 13/00
[52] U.S. Cl. ......................... 128/899; 128/897; 128/898; 424/423; 424/424; 424/425
[58] Field of Search ..................................... 424/422, 423, 424/424, 425, 426; 514/810–13; 128/898, 899, 897; 607/58

[56] References Cited

U.S. PATENT DOCUMENTS

| 5,486,362 | 1/1996 | Kitchell et al. ........................ 424/426 |
| 5,573,528 | 11/1996 | Aebischer et al. .................. 604/891.1 |
| 5,618,287 | 4/1997 | Fogarty et al. ........................ 606/129 |

*Primary Examiner*—Thurman K. Page
*Assistant Examiner*—Kathryne E. Shelborne
*Attorney, Agent, or Firm*—Birch, Stewart, Kolasch & Birch, LLP

[57] ABSTRACT

The invention refers to a solution of the problem to induce alcoholics or other drug abusers to refrain from alcohol or other drug during a longer period of time. Thus it consists of an implantable device for preventing a person from using a drug, which includes means to detect the drug in question in the body of the person or a substance that is dependent of the existence of the drug and means thereby to emit a preparation stored in the device or electric pulses with such effect and dosage that negative reactions are brought about in the person.

9 Claims, 1 Drawing Sheet

IMPLANTABLE DEVICE

The present invention refers to a device for preventing a person from using a drug. The invention in particular refers to an implantable device In order to dispense a preparation stored in the device with such effect and dosage that negative reactions are obtained in the person. The device includes means for sensing the presence of the drug or a substance associated with the drug in the body and control of the dispensing of the preparation so that it is dispensed only after the presence of the drug has been detected. The invention is especially adapted for implantation on alcoholics with the purpose of completely prevent the use of alcohol, whereby the preparation normally never is dispensed to the body since the knowledge about its effect makes the person to completely relinquish alcohol.

An object of the present invention is thus to provide a device that constitutes an efficient hindrance for an abuser to exert his abuse. It is also an object to provide a device of the type being operative during a long period of time and which can not be manipulated or removed by the addict.

A further object is that the device should not dispense any preparation when a drug or the like is not detected, whereby side effects of long term use of chemical preparations is eliminated. Still an object is to utilize the knowledge of the abuser about the function and effect of the device so that the person does not exert the abuse and the device will not be activated. These and other objects are accomplished by giving a device according to the invention the features stated in the subsequent patent claims.

The invention will now be described in closer detail with reference to the drawing on which FIG. 1 diagrammatically shows an example of a device according to the invention.

The device is constructed in a way similar to the implantable insulin pumps that sense the sugar content of the blood and dispenses insulin so that this content is maintained within a definite interval, but in comparison to these it exhibits substantial differences in function and area of use. A substantial difference is that the substance that is sensed is of the kind that normally should not be present in the body, such as alcohol or another drug or any substance that is associated with the existence of such a drug. Another substantial difference is that the preparation which is stored in the device in order to be dispensed if necessary is not intended to restore an imbalance in the body but instead brings about such a discomfort in the form of nausea and similar negative reactions that the person quickly stops taking the drug and avoids it henceforth.

BRIEF DESCRIPTION OF DRAWING

An embodiment according to FIG. 1 of a device according to the invention consequently exhibits an implantable housing 1 provided with a sensor means 2 and an output orifice 3 for a preparation stored in the device. The sensor means 2 can be placed on the outside of the housing 1 or at the end of a longish means (not shown) connected to the housing, whereby the sensor means for instance can be applied in a vein, in the subcutis fat or in the abdominal cavity. The sensor means 2 in the housing 1 is connected to a sensing circuit 4. This interacts with the sensor means in such a way that an output signal which is dependent of the drug sensed in the present case by the sensor is emitted from the sensing circuit 4. When a threshold value of the output signal is exceeded, which is detected by the threshold value circuit 5, this gives an output signal to a pump control circuit 6 which connects the pump 7 so that it emits a predetermined amount of the preparation from a container 8 through the output orifice 3, which is arranged to dispense the preparation in the tissue around the housing 1 or to a catheter (not shown) that ends in a vessel or in another part of the tissue The device according to the invention is preferably also provided with an energy source 9 and a control unit 10 with a clock that controls the energy supply to the circuits so that they are only switched in at a predetermined interval and inbetween do not use any energy. An extra delay is also provided to be activated after the pump 7 has been connected so that a new dose of the preparation can be dispensed only alter a longer period of time when the effect of a first dose has declined, so that no overdose of the preparation can be dispensed.

The device according to the invention is especially intended for alcoholics. The sensor means and the sensing circuit thereby are arranged to sense the concentration of alcohol in the blood or other body fluid and they can be constituted by in principle known devices for this purpose. The preparation that is dispensed may incorporate the active component disulfiram in conformity with preparations with the well-known trade name "Antabuse™", registered by the drug company Dumex. It may also contain calcium carbimide as in "Dipsan" registered by Lederle.

Figure 1:
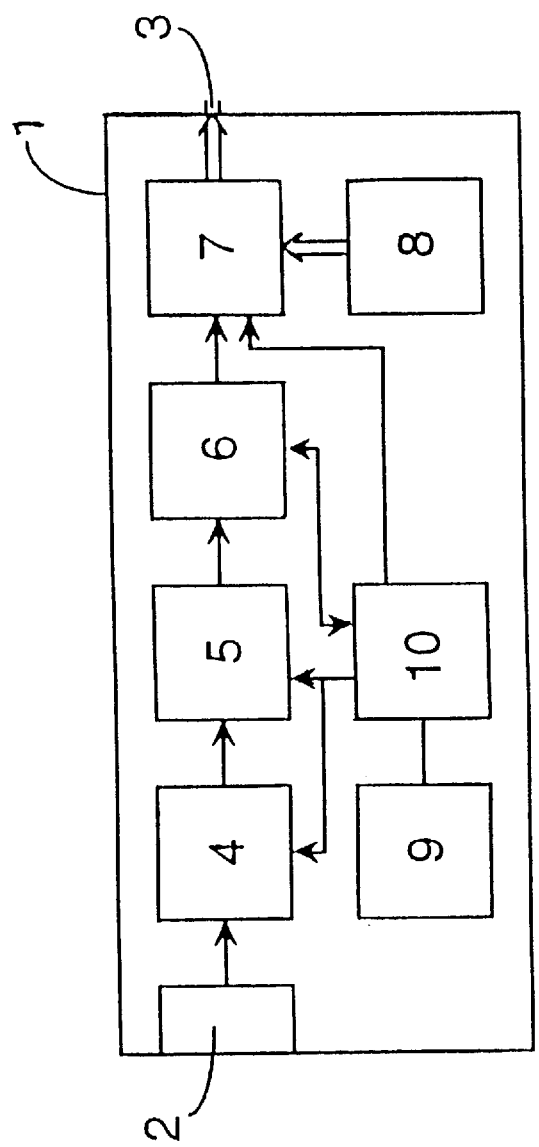

The reaction of the body on these drugs in combination with alcohol is well-known. An advantage of the alcohlic having a device according to the invention implanted is that no preparation is dispensed as long as no alcohol is dejected in the blood and that thereby no side effects of the preparation may arise. Another advantage with this type of preparation is also that they do not give any effect if they due to malfunction come out in the body when no alcohol has been consumed. The knowledge that it is not possible to escape the effects of the preparation also results in that practically no attempts to or mistakes with consumption of alcohol will occur, and this effect with an implanted device can be achieved during a long period of time, at least equal to the life-span of the batteries which may amount to several years.

It is also possible for alcohlics or other drug abusers to utilize other preparations than disulfiram and calcium carbimide in the device. These should have the effect that the person much unwillingly exposes himself to it, but the effect can be obtained by the preparation alone, since it by the device only is pumped into the body after use of alcohol or other drug that is detected by the device.

By utilization of the invention in connection with abuse of other drugs than alcohol, at it arranged to detect the drug or any substance related to the drug instead of alcohol. In this case the preparation, being dispensed should not be disulfiram or calcium carbimide, since these substances require presence of alcohol in order to give unpleasant and negative reactions to the person.

As an alternative to create unpleasant reactions by means of a chemical preparation pulses from an electric stimulator circuit built into the device is utilized instead. The container of the preparation, the pump and the preparation orifice or the catheter thereby are exchanged for a battery which can be same as that used in the remaining circuits, an electric stimulator circuit and electrodes, one of which can be provided on the housing and one or more in the tissue that is going to be stimulated. The stimulation technique in itself is known from pacemakers, defibrillators and so on. In this application the strength of the stimulation signals and the location of the electrodes is adapted so that as far as possible a harmless but strong reaction of the type muscular spasm or the like is obtained, which recurs with predetermined intervals as long as the drug is detected, possibly the strength may be dependent of the sensed content.

Other embodiments of the invention are also possible within the scope of the subsequent patent claims.

What is claimed is:

1. An implantable device for preventing a person from using a drug, comprising
   a means to detect the drug in question in the body of the person or a substance that is dependent of the existence of the drug; and
   a means to dispense a preparation stored in the device or emit electric pulses from a stimulator in the device with such effect and dosage that negative reactions are brought about in the person,
   wherein said means to detect the drug comprises a sensor means (2) connected to a sensing circuit (4) which interacts with the sensor means in such a way that an output signal is emitted from the sensing circuit (4) which is dependent of the drug sensed by the sensor, and a threshold value circuit (5) which detects when a threshold value for the output signal from the sensing circuit (4) is exceeded and gives an output signal to means to bring about negative reactions in the person.

2. The device according to claim 1, wherein the dispensing of the preparation stored in the device is carried out with a predetermined dose and the device is turned off or obstructed from dispensing of a new dose during a predetermined time period after.

3. The device according to claim 1 or 2, wherein the drug is constituted by alcohol and the active component of the preparation is constituted by disulfiram, calcium carbimide or agent with a similar effect.

4. The device according to claim 1 or 2, wherein the drug is constituted by alcohol and the preparation is such that negative reactions are brought about to the person even without the influence of alcohol.

5. The device according to claim 1, wherein the means to bring about negative reactions include a pump control circuit (6) that turns on a pump (7) so that it dispenses a predetermined amount of the preparation from a container (8) through an output orifice (3).

6. The device according to claim 1, wherein the means to bring about negative reactions include an electric stimulator circuit which emits electric pulses to electrodes outside the device.

7. The device according to claim 6, wherein the preparation is dispensed to a catheter which ends in a vessel or in another part of the tissue.

8. A method of detecting the existence of a substance in the body and in dependence thereof dispensing a preparation stored in the device or electric pulses generated in the device, in order to sense a drug and dispense a preparation or emit electric pulses intended to bring about negative reactions in the person comprising implanting a device of claim 1 in the body of a person.

9. The method according to claim 9, wherein the drug is alcohol and the active constituent of the preparation is disulfiram or calcium carbimide.

* * * * *